United States Patent
Wilson et al.

(10) Patent No.: US 10,034,989 B2
(45) Date of Patent: Jul. 31, 2018

(54) BLISTER PIERCING ELEMENT FOR A DRY POWDER INHALER

(71) Applicant: VECTURA DELIVERY DEVICES LIMITED, Chippenham (GB)

(72) Inventors: Peter Wilson, Cambridgeshire (GB); Andreas Meliniotis, Cambridgeshire (GB)

(73) Assignee: VECTURA DELIVERY DEVICES LIMITED, Chippenham, Wiltshire (GB)

(*) Notice: Subject to any disclaimer, the term of this patent is extended or adjusted under 35 U.S.C. 154(b) by 642 days.

(21) Appl. No.: 14/760,200

(22) PCT Filed: Jan. 17, 2014

(86) PCT No.: PCT/GB2014/050132
§ 371 (c)(1),
(2) Date: Jul. 9, 2015

(87) PCT Pub. No.: WO2014/114916
PCT Pub. Date: Jul. 31, 2014

(65) Prior Publication Data
US 2015/0335833 A1    Nov. 26, 2015

(30) Foreign Application Priority Data

Jan. 23, 2013 (GB) .................................. 1301192.9

(51) Int. Cl.
*A61M 15/00* (2006.01)

(52) U.S. Cl.
CPC ...... *A61M 15/0035* (2014.02); *A61M 15/004* (2014.02); *A61M 15/0021* (2014.02);
(Continued)

(58) Field of Classification Search
CPC .......... A61M 15/0033; A61M 15/0035; A61M 15/0036; A61M 15/0038; A61M 15/004; A61M 15/0041
See application file for complete search history.

(56) References Cited

U.S. PATENT DOCUMENTS 2,013,328 A * 9/1935 Wiswell .................... B67B 7/28
222/536
4,357,753 A * 11/1982 Wilkinson ................ B67B 7/24
30/443
(Continued)

FOREIGN PATENT DOCUMENTS

CN    1216928    5/1999
CN    1867369    11/2006
(Continued)

OTHER PUBLICATIONS

Search Report issued in connection with corresponding British Application No. GB1301192.9, dated May 8, 2013.
(Continued)

*Primary Examiner* — Kathryn E Ditmer
(74) *Attorney, Agent, or Firm* — Davidson, Davidson & Kappel, LLP

(57) ABSTRACT

A blister piercing element for puncturing the lid of a blister containing a dose of medicament for inhalation by a user is disclosed. It comprises a body having a surface and an opening in the surface for the passage of air, or for the passage of medicament entrained in air, through the body. The body includes a pair of spaced cutting teeth upstanding from the surface in spaced side-by-side relation, each cutting tooth projecting in cantilevered form over said opening and each having a distal cutting edge at a free end remote from said surface. The distal cutting edge of each tooth is configured to initiate a slit in a blister lid when pressure is applied to a blister lid by the teeth and the teeth are spaced (Continued)

from each other so that separate slits cut by the distal cutting edge of each tooth propagate in a direction toward each other between the teeth as the teeth continue to penetrate a blister lid. The pair of spaced cutting teeth form a single slit in a blister lid that defines a single flap which is folded into the blister by the teeth.

14 Claims, 4 Drawing Sheets

(52) U.S. Cl.
CPC .... *A61M 15/0038* (2014.02); *A61M 15/0041* (2014.02); *A61M 15/0051* (2014.02); *A61M 15/0045* (2013.01); *A61M 15/0091* (2013.01); *A61M 2202/064* (2013.01); *A61M 2205/8225* (2013.01); *A61M 2205/8275* (2013.01); *A61M 2210/0618* (2013.01); *A61M 2210/0625* (2013.01)

(56) References Cited

U.S. PATENT DOCUMENTS

| | | | |
|---|---|---|---|
| 4,627,432 A | 12/1986 | Newell et al. | |
| 4,678,106 A | 7/1987 | Newell et al. | |
| 4,811,731 A | 3/1989 | Newell et al. | |
| 4,826,492 A | 5/1989 | Magasi | |
| 5,035,237 A | 7/1991 | Newell et al. | |
| 5,312,422 A | 5/1994 | Trott | |
| 5,533,502 A | 7/1996 | Piper | |
| 5,542,411 A | 8/1996 | Rex | |
| 5,617,971 A | 4/1997 | Eason et al. | |
| 5,769,073 A | 6/1998 | Eason et al. | |
| 5,785,049 A | 7/1998 | Smith et al. | |
| 5,848,996 A | 12/1998 | Eldor | |
| 5,875,776 A | 3/1999 | Vaghefi | |
| 5,881,719 A | 3/1999 | Gottenauer et al. | |
| 6,045,004 A * | 4/2000 | Elliott | B65D 47/0804 222/494 |
| 6,089,228 A | 7/2000 | Smith et al. | |
| 6,401,712 B1 * | 6/2002 | von Schuckmann | A61J 1/035 128/203.12 |
| 6,543,448 B1 | 4/2003 | Smith et al. | |
| 7,070,583 B1 | 7/2006 | Higuchi et al. | |
| 2001/0029948 A1 | 10/2001 | Ingle et al. | |
| 2002/0124846 A1 | 9/2002 | Ekelius et al. | |
| 2003/0150453 A1 | 8/2003 | Edwards et al. | |
| 2004/0154619 A1 | 8/2004 | Edwards et al. | |
| 2004/0236282 A1 | 11/2004 | Braithwaite | |
| 2005/0161041 A1 | 7/2005 | Schuler et al. | |
| 2006/0178646 A1 | 8/2006 | Harris et al. | |
| 2006/0185672 A1 | 8/2006 | Pinon et al. | |
| 2006/0200095 A1 | 9/2006 | Steube | |
| 2006/0212004 A1 | 9/2006 | Atil | |
| 2006/0254583 A1 | 11/2006 | Deboeck et al. | |
| 2007/0074721 A1 | 4/2007 | Harmer et al. | |
| 2007/0137645 A1 | 6/2007 | Eason et al. | |
| 2008/0184998 A1 | 8/2008 | Myrman et al. | |
| 2009/0090362 A1 * | 4/2009 | Harmer | A61M 15/0045 128/203.21 |
| 2009/0250057 A1 * | 10/2009 | Wachtel | A61M 15/0045 128/203.15 |
| 2010/0108058 A1 | 5/2010 | Glusker et al. | |
| 2010/0192949 A1 | 8/2010 | Wright et al. | |
| 2010/0300441 A1 | 12/2010 | Von Schuckmann et al. | |
| 2011/0120463 A1 | 5/2011 | Esteve et al. | |
| 2011/0259328 A1 | 10/2011 | Villax et al. | |
| 2015/0343159 A1 * | 12/2015 | Farr | A61M 15/0026 128/203.15 |

FOREIGN PATENT DOCUMENTS

| | | | |
|---|---|---|---|
| CN | 101124006 | 2/2008 | |
| DE | 19502725 | 8/1996 | |
| DE | 102009041664 A1 * | 3/2011 | ........ A61M 15/0028 |
| EP | 0129985 | 1/1985 | |
| EP | 0491426 | 6/1992 | |
| EP | 0525720 | 2/1993 | |
| EP | 1132104 | 9/2001 | |
| EP | 1386630 | 2/2004 | |
| EP | 2082769 | 7/2009 | |
| EP | 2198907 | 6/2010 | |
| EP | 2210638 | 7/2010 | |
| GB | 1472650 | 5/1977 | |
| GB | 2246299 | 1/1992 | |
| GB | 2264237 | 8/1993 | |
| GB | 2340758 | 3/2000 | |
| GB | 2405798 | 3/2005 | |
| GB | 2407042 | 4/2005 | |
| GB | 2420982 | 6/2006 | |
| GB | 2439204 | 12/2007 | |
| GB | 2467388 | 8/2010 | |
| JP | A-62-281959 | 12/1987 | |
| JP | 05200100 | 8/1993 | |
| JP | 2009-510367 | 10/1997 | |
| JP | A-2002-248094 | 9/2002 | |
| JP | 2005-509460 | 4/2005 | |
| JP | 2006-502759 | 1/2006 | |
| JP | 2006-508699 | 3/2006 | |
| RU | 2091088 | 9/1997 | |
| RU | 2146153 | 3/2000 | |
| RU | 2148417 | 5/2000 | |
| RU | 2158609 | 11/2000 | |
| TW | 201141557 | 12/2011 | |
| WO | WO90/13328 | 11/1990 | |
| WO | WO91/06333 | 5/1991 | |
| WO | WO95/06491 | 3/1995 | |
| WO | WO95/31238 | 11/1995 | |
| WO | WO96/09085 | 3/1996 | |
| WO | WO9727892 | 8/1997 | |
| WO | WO01/26720 | 4/2001 | |
| WO | WO01/43802 | 6/2001 | |
| WO | WO01/85097 | 11/2001 | |
| WO | WO01/87393 | 11/2001 | |
| WO | WO02/02161 | 1/2002 | |
| WO | WO03080163 | 10/2003 | |
| WO | WO2005/025656 | 3/2005 | |
| WO | WO2005/037353 | 4/2005 | |
| WO | WO2006/108877 | 10/2006 | |
| WO | WO 2006/108877 | 10/2006 | |
| WO | WO2007/098870 | 9/2007 | |
| WO | WO2008/051621 | 5/2008 | |
| WO | WO2009/004465 | 1/2009 | |
| WO | WO2009065707 | 5/2009 | |

OTHER PUBLICATIONS

International Search Report issued in connection with corresponding PCT Application No. PCT/GB2014/050132, dated Mar. 27, 2014.

* cited by examiner

BLISTER PIERCING ELEMENT FOR A DRY POWDER INHALER

This application is a national phase application under 35 U.S.C. § 371 of International Application No. PCT/GB2014/050132, filed Jan. 1, 2014, which claims priority to GB 1301102.9, filed on Jan. 23, 2013, the disclosures of which are all hereby incorporated by reference herein.

FIELD OF THE INVENTION

The present invention relates to a blister piercing element for a dry powder inhalation device. In particular, it relates to a piercing element for puncturing the foil lid of a blister that contains an individual dose of medicament for inhalation by a user of the inhalation device.

BACKGROUND

Oral or nasal delivery of a medicament using an inhalation device is a particularly attractive method of drug administration as these devices are relatively easy for a patient to use discreetly and in public. As well as delivering medicament to treat local diseases of the airway and other respiratory problems, they have more recently also been used to deliver drugs to the bloodstream via the lungs, thereby avoiding the need for hypodermic injections.

It is common for dry powder formulations to be pre-packaged in blisters each of which contains a single dose of powder which has been accurately and consistently measured. The blister protects each dose from the ingress of moisture and penetration of gases such as oxygen in addition to shielding the dose from light and UV radiation all of which can have a detrimental effect on the medicament and on the operation of an inhaler used to deliver the medicament to a patient.

A blister pack generally comprises a base having one or more spaced apart cavities defining blisters to receive individual doses of medicament and a lid in the form of a generally planar sheet that is sealed to the base except in the region of the cavities. The base material is typically a laminate comprising a polymer layer in contact with the drug, a soft tempered aluminium layer and an external polymer layer. The aluminium provides the moisture and oxygen barrier, whilst the polymer aids adhesion of the aluminium to the heat seal lacquer and provides a relatively inert layer in contact with the drug. Soft tempered aluminium is ductile so that it can be "cold formed" into a blister shape. It is typically 45 μm thick. The outer polymer layer provides additional strength and toughness to the laminate.

The lid material is typically a laminate comprising a heat seal lacquer, a hard rolled aluminium layer and an external lacquer layer. The heat seal lacquer layer bonds to the polymer layer of the base foil laminate during heat-sealing to provide a seal around the top of the blister cavity. The hard temper foil is relatively frangible to enable it to be pierced easily by a piercing element forming part of an inhalation device, to create one or more openings in the lid. These openings enable air or gas to flow through the blister, thereby entraining the dry powder and causing it to be removed from the blister. The powder can then be deagglomerated to form a respirable cloud and made available for inhalation by the user.

Inhalation devices that receive a blister pack or strip of blisters are known. Actuation of the device causes a mechanism to index and pierce a blister so that when the device is used, air is drawn through the blister entraining the dose, which is then carried out of the blister through the device and via the patient's airway down into the lungs. One such device is known from one of the Applicant's own European patent No. 1684834B1, which is incorporated in its entirety herein by reference.

The airflow can be created by inhalation of the user. Such inhaler devices are generally known as passive devices. Alternatively, the inhaler may include a source of energy such as a mechanical pump or canister of pressurised gas to generate pressure or suction. The air or gas flow in these active devices can potentially be greater than that in a passive device, and more repeatable. This can give better and more consistent blister emptying.

It has been found that it is difficult to control the size and configuration of the opening that is pierced in a blister lid because the foil may not always tear or burst in a consistent way. However, the means by which the blister is pierced is of critical importance in the performance of a dry powder inhalation device.

It is common for problems to occur because, when the lid is pierced, foil flaps are formed that are pushed into the blister. These can either trap powder in the blister or obscure the opening. It will be appreciated that it is beneficial to form a large opening in the blister lid to enable a sufficient flow of air through the blister, and to enable the removal of agglomerates that may have formed in the powder during storage. However, a large opening in the blister means that the foil flaps are large and so are more likely to trap powder and hinder airflow. Furthermore, more powder may be trapped depending upon the orientation in which the device is being held when piercing takes place.

Although the Applicant's own earlier application EP1868674A, which is incorporated herein by reference, provides a blister piercing member that addresses the problem of powder being trapped in the blister by a foil flap cut in the blister lid, many powders are particularly cohesive in nature and form agglomerates in the blister that can still become trapped more easily than less cohesive powders where agglomerates are less easily formed. Therefore, there is a desire to further minimise the possibility of powder becoming trapped behind a foil flap, particularly when the dose is formed from a more cohesive powder that is more likely to agglomerate. There is also a desire to provide a blister piercing element which provides a more consistent pierce and in which the likelihood of powder becoming trapped is less dependent on the orientation in which the inhaler is in when piercing occurs.

SUMMARY OF THE INVENTION

The present invention seeks to provide a blister piercing element that ensures a smooth flow of air through the blister and avoids or reduces the amount of powder that may become trapped behind foil flaps created in the blister lid when the blister lid is pierced.

According to the invention, there is provided a blister piercing element for puncturing the lid of a blister containing a dose of medicament for inhalation by a user, said blister piercing element comprising a body having a surface and an opening in the surface for the passage of air, or for the passage of medicament entrained in air, through the body, wherein the body includes a pair of spaced cutting teeth upstanding from the surface in spaced side-by-side relation, each cutting tooth projecting in cantilevered form over said opening and each having a distal cutting edge at a free end remote from said surface, the distal cutting edge of each tooth being configured to initiate a slit in a blister lid when pressure is applied to a blister lid by the teeth, the teeth being spaced from each other so that separate slits cut by the distal cutting edge of each tooth propagate in a direction toward each other between the teeth as the teeth continue to penetrate a blister lid, said pair of spaced cutting teeth forming a single slit in a blister lid that defines a single flap which is folded into the blister by the teeth.

As only a single flap is formed as a result of using this piercing element, there is less chance for powder to become trapped than if there are multiple flaps.

In one embodiment, each tooth comprises an upright portion extending from the surface adjacent to, or from, a periphery of the opening and a cantilevered portion that extends from an upper end of the upright portion and projects out over said opening.

Preferably, the teeth are symmetrical about a line extending between the teeth.

In some embodiments, the opening has first and second opposite edges and the teeth upstand from the surface adjacent to the first edge and project in cantilevered form in a direction towards the second edge to an extent that the distal cutting edge is closer to the second edge than to the first edge.

Preferably, each tooth comprises an apex that lies on the distal cutting edge and which initially punctures a blister lid, said distal cutting edge extending away from the apex of each tooth in both directions and at an angle towards the surface.

A first part of the distal cutting edge of each tooth may extend from the apex in a direction toward the apex of the other tooth.

Preferably, said first distal cutting edge parts of each tooth are configured so that a slit cut by the first distal cutting edge part of each tooth propagate toward each other as the teeth penetrate a blister lid to form a single slit extending between the apex of each tooth.

In a preferred embodiment, said first distal cutting edge part of each tooth are configured so that the slit extending between the apex of each tooth is linear.

Preferably, a second part of the distal cutting edge of each tooth extends from the apex in a direction away from the other tooth.

A secondary cutting edge preferably extends from the apex of each tooth along the cantilevered portion towards the upright portion. The secondary cutting edge may extend from the apex at an angle towards the surface.

Preferably, the secondary cutting edges of respective teeth extend at an angle away from each other.

Each tooth may have a first angled facet bound by said first part of the distal cutting edge extending from the apex of a tooth towards the other tooth, and its secondary cutting edge.

Each tooth may also have a second angled facet bound by said second part of the distal cutting edge extending from the apex of a tooth in a direction away from the other tooth, and its secondary cutting edge.

Preferably, the first part of the distal cutting edge of each tooth extends from the apex towards said surface at an angle which is shallower than the angle at which the second part of the distal cutting edge of each tooth extends from the apex towards said surface.

In a preferred embodiment, the opening in the surface comprises a first opening and the pair of spaced cutting teeth comprise a first pair of spaced cutting teeth, the body comprising a second opening in the surface, a second pair of spaced cutting teeth upstanding from the surface in spaced side-by-side relation, each cutting tooth of the second pair projecting in a cantilevered form over said second opening and each having a distal cutting edge at a free end remote from said surface, the distal cutting edge of each second tooth being configured to initiate a slit in a blister lid when pressure is applied to a blister lid by the second teeth at the same time pressure is applied to a blister lid by the first teeth, the second teeth being spaced from each other so that a slit cut by the distal cutting edge of each second tooth propagates in a direction toward each other between the second teeth as the second teeth continue to enter the blister so that a single slit is formed in the blister lid by said second pair of spaced cutting teeth that defines a single flap that is folded into the blister by the second teeth.

Preferably, the first and second pairs of spaced cutting teeth are positioned in back-to-back relation so that the first pair of spaced cutting teeth project in cantilevered form over the first opening in an opposite direction to the direction in which the second pair of spaced cutting teeth project in cantilevered form over the second opening.

The body may be configured so that the first opening forms a passage for the flow of air through the body and into a pierced blister and the second opening forms a passage for the flow of air and medicament entrained in said air out of said pierced blister.

Embodiments of the present invention will now be described, with reference to the accompanying drawings, in which:

DETAILED DESCRIPTION

Figure 1:
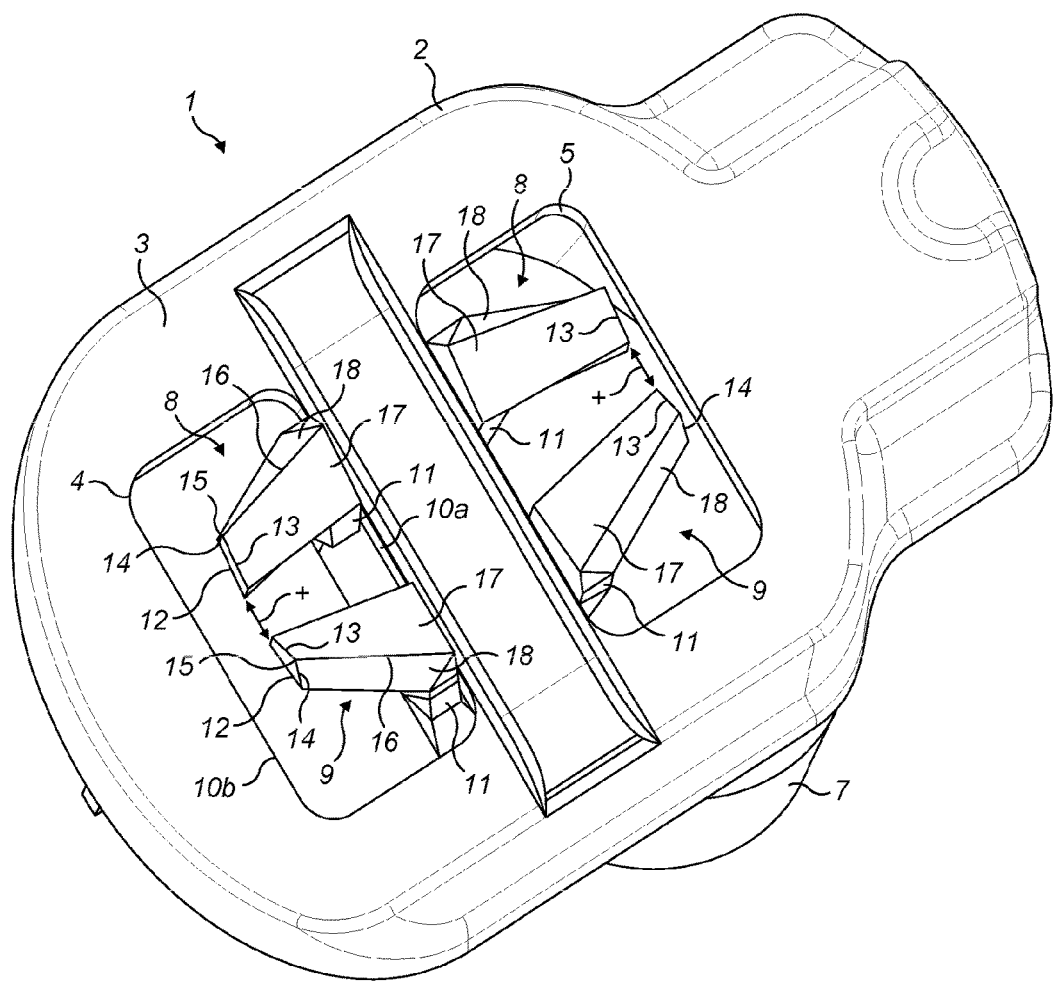
FIG. 1 is an enlarged perspective view of a blister piercing element according to an embodiment of the invention.
Figure 2:
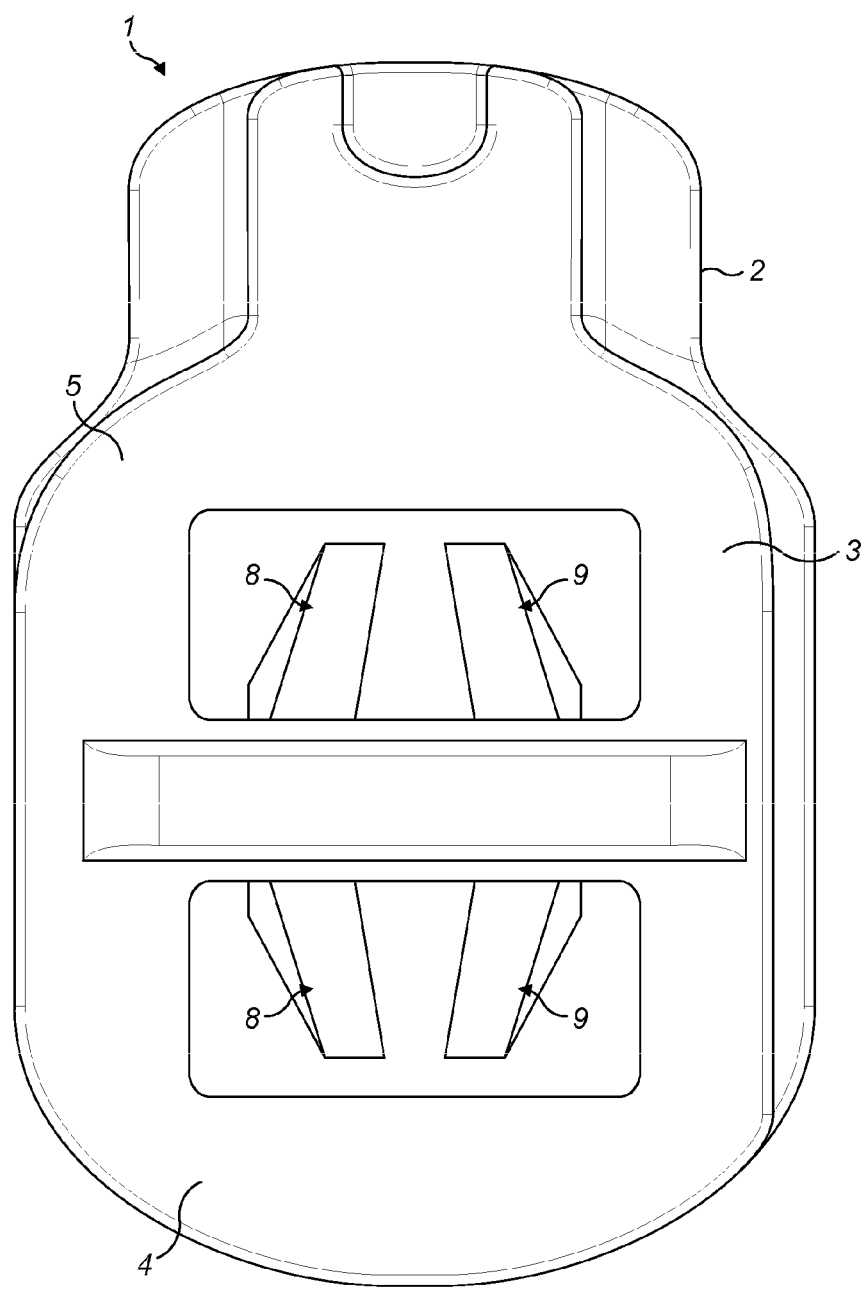
FIG. 2 is an enlarged top plan view of the blister piercing element shown in FIG. 1.
Figure 3:
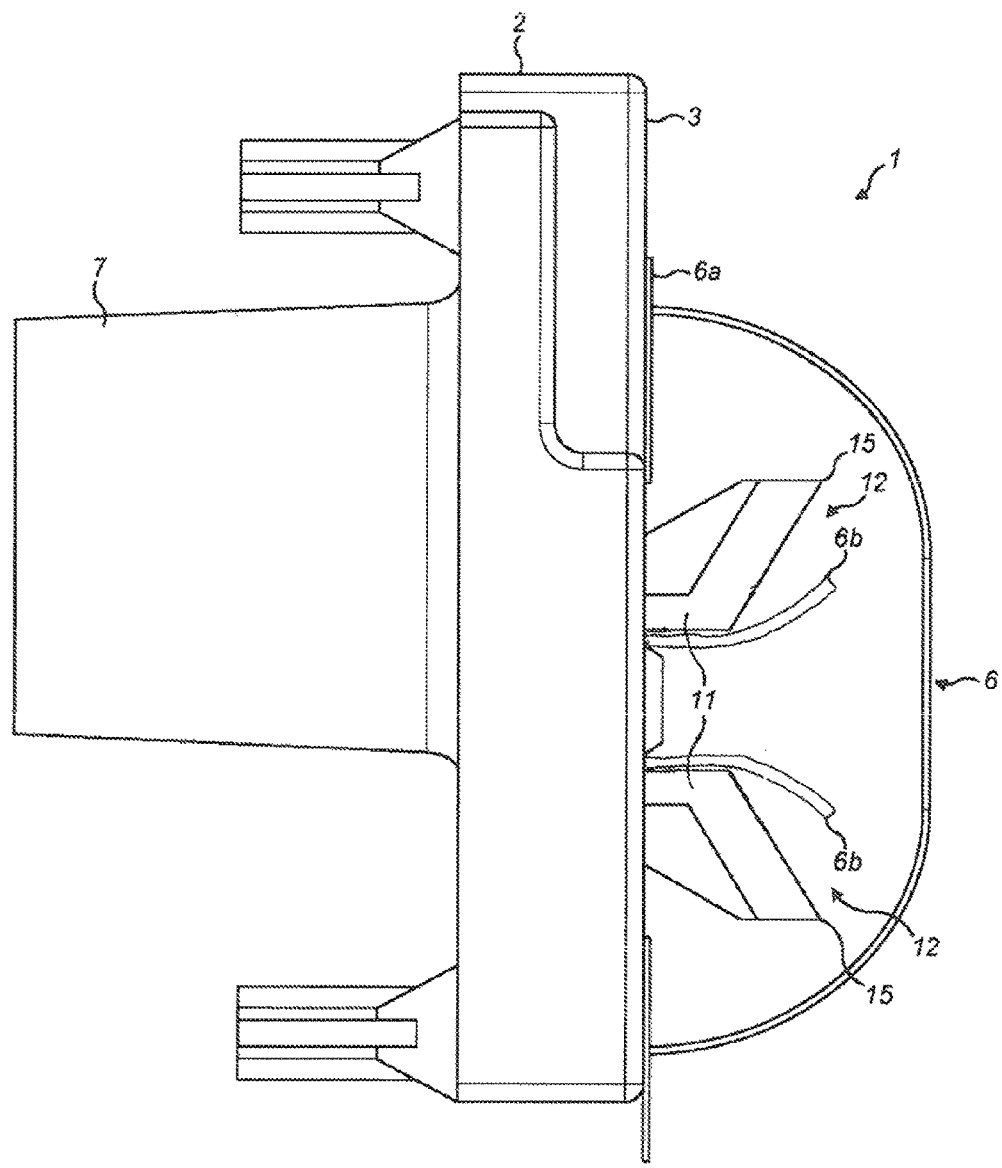
FIG. 3 is an enlarged side elevation of the blister piercing element shown in FIGS. 1 and 2 but in a position in which a blister has been pierced and showing a blister in outline.
Figure 4:
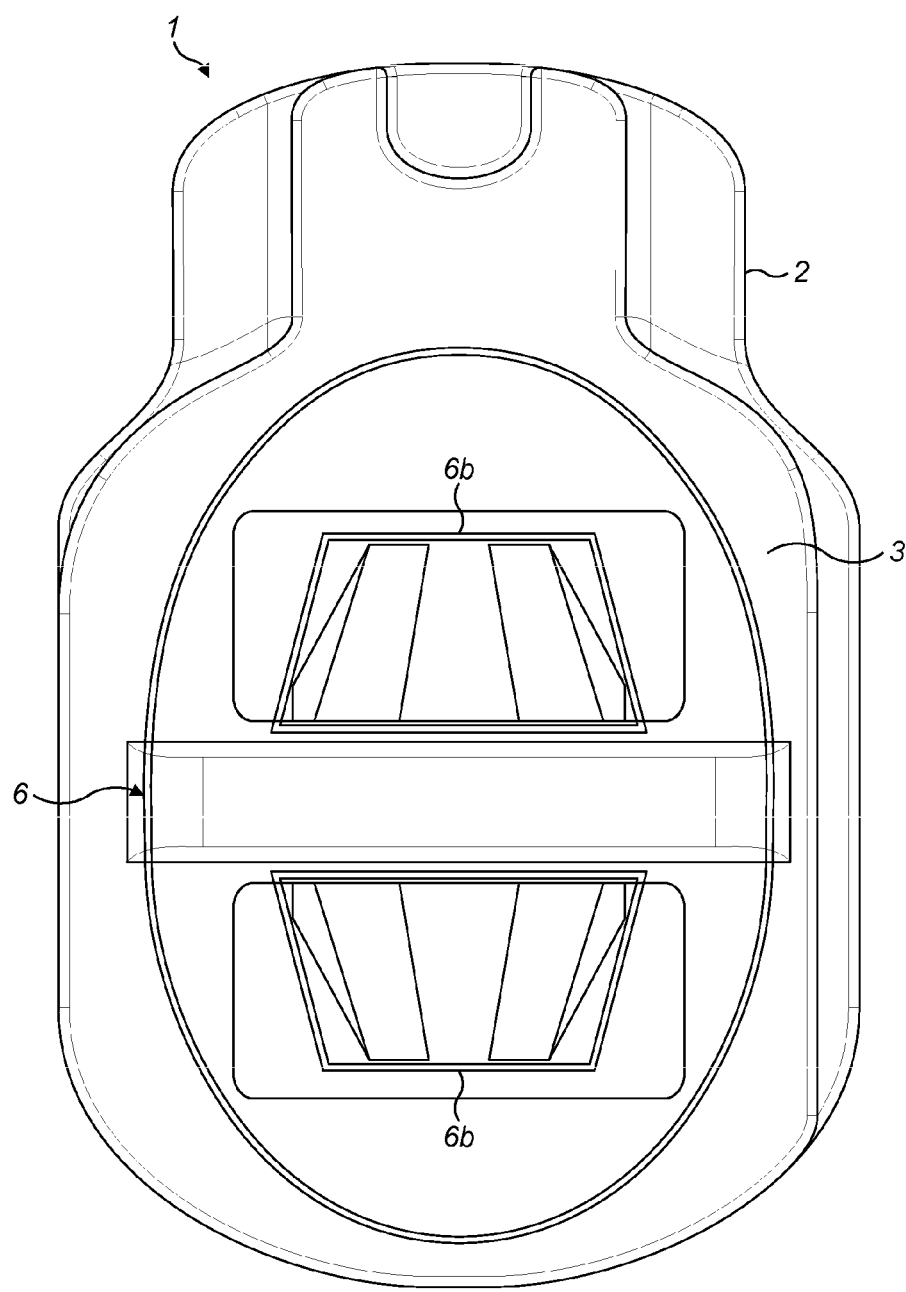
FIG. 4 is a top plan view of the blister piercing element and blister outline shown in FIG. 3.

Referring now to FIGS. 1 to 4 and to FIG. 1 in particular, there is shown a blister piercing element 1 according to an embodiment of the present invention comprising a body 2 having a blister lid facing surface 3 with first and second openings 4, 5 therein. First opening 4 forms a clean, non-drug laden airflow path into a pierced blister 6 (see FIGS. 3 and 4) whereas second opening 5 forms a drug laden airflow path out of a blister 6. The body 2 has a flow channel 7 extending from the second opening 5 to direct drag laden air that has passed through the second opening 5 into a mouthpiece of a dry powder inhalation device (not shown).

A pair of adjacent teeth 8, 9 positioned in spaced side-by-side relation upstand from the edge or periphery 10 of the first aperture 4 and overhangs the first opening 4. Each tooth 8, 9 is symmetrical about a plane extending between the teeth 8,9 which is perpendicular to the surface 3. Each tooth 8, 9 has a generally upright base portion 11 that upstands from the surface 3 of the body 2. A cantilevered portion 12 extends from the upright base portion 11 and has a free end that is suspended over the first opening 4. The cantilevered portion 12 is therefore supported only at one end by the upright base portion 11 and extends out over the first opening 4 without any other means of support.

The opening 4 may have first and second opposing edges 10a, 10b with the base portion 11 of each tooth 8,9 extending upwardly from the first edge 10a. The cantilevered portion 12 then extends from the top of the base portion 11 across the opening 4 for at least half the distance between the first and second opposing edges 10a, 10b and, preferably, for at least two-thirds of the distance between the first and second opposing edges 10a, 10b.

A distal primary cutting edge 13, 14 is formed at the free end of each cantilevered portion 12. An apex 15 lies on the distal cutting edge 13, 14 and a first distal cutting edge part 13 extends from the apex 15 of each tooth 8, 9 in a direction towards the apex 15 of the other tooth 8,9. The apex 15 represents the highest point of each tooth 8,9 from the surface 3 of the body 2 and the first distal cutting edge parts 13 are angled away from the apex 15 in a direction towards the surface 3. As the teeth 8, 9 are spaced from each other, the first distal cutting edge parts 13 of each tooth 8, 9 do not meet each other but are spaced by a distance ("X" in FIG. 1) between them. If a straight line were to be drawn from the apex 15 of one tooth 8, 9 to the apex 15 of the other tooth 8, 9, the first distal cutting edge parts 13 would lie on the same line, i.e. the first distal cutting edge parts 13 are in linear alignment with each other.

A second cutting edge part 14 extends away from each apex 15 in an opposite direction to the first cutting edge part 13. The second cutting edge part 14 is also angled away from the apex 15 in a direction towards the surface 3, but the angle is steeper than the angle at which the first cutting edge parts 13 extend relative to the surface 3. If the aforementioned line were to be extended beyond the apex 15 of each tooth 8,9 in each direction, then the second distal cutting edge parts 14 would also lie on the same line, i.e. the first and second distal cutting edge parts 13,14 are all in linear alignment with each other.

A secondary cutting edge 16 extends from the apex 15 along the length of the cantilevered portion 12 towards the upright 11. The secondary cutting edge 16 is also angled away from the apex 15 in a direction towards the surface 3.

Each tooth 8,9 has a first angled facet or face 17 which is bound by the first primary cutting edge part 13 and the secondary cutting edge 16, both of which extend from the apex 15. A second angled facet 18 is bound by the second primary cutting edge part 14 and the secondary cutting edge 16. The second angled facet 18 is angled towards the surface 3 at an angle which is steeper than the angle at which the first angled facet 17 is angled towards the surface 3.

As shown in FIG. 1, there are two adjacent openings 4, 5, each opening 4, 5 having a pair of teeth 8, 9 that have the same form as described above. The pair of teeth 8, 9 associated with one opening 4 are arranged in back-to-back relation to the pair of teeth 8, 9 associated with the other opening 5. However, in an alternate embodiment, there may be only one opening in the body and one pair of teeth 8, 9 associated with that opening or, two openings 4, 5 but one opening may alternatively be provided with a different form of teeth or piercer.

When the piercing element as shown in FIG. 1 is mounted in a dry powder inhalation device and the device is operated to pierce a blister lid, the surface 3 of the body 2 is moved towards a lid 6a (see FIG. 3) of a blister 6 to be pierced. Ideally, the piercing element 1 is moved towards the blister lid 6a so that the surface 3 and the plane of the blister lid 6a remain parallel to each other, although the piercing element 1 may be pivotally mounted, in which case it will not be perfectly parallel to the plane of the blister lid 6a as it begins to enter the blister lid 6a.

The apex 15 of each tooth 8, 9 makes an initial incision in the blister lid 6a as the apex 15 is at the furthest distance from the surface 3. As the teeth 8, 9 penetrate further through the blister lid 6a, the distal cutting edge 13, 14 of each tooth 8, 9 forms a slit. The first part 13 of the distal cutting edge forms a slit that extends from the apex 15 in a direction towards the apex 15 of the other tooth 8, 9 and the secondary cutting edge 16 of each tooth 8, 9 cuts a slit extending in a direction away from the apex 15 along the cantilevered portion 12 towards the edge of the blister lid 6a from which the tooth 8, 9 upstands. As the teeth 8, 9 continue to penetrate the blister lid 6a, the slit formed by the first part 13 of the distal cutting edge of each tooth 8, 9 propagates or bursts across the gap "X" so as to join up the slits formed by each first distal cutting edge part 13 so that a single continuous slit formed by the secondary cutting edges 16 and the first part of the distal cutting edges 13 of each tooth 8, 9 is created. As the teeth 8, 9 penetrate further through the lid 6a of a blister, a single flap 6b is formed which is folded into the blister 6 by the teeth 8, 9.

A variety of medicaments may be administered alone by using an inhaler incorporating a blister piercing element according to the invention. Such medicaments include those that are suitable for the treatment of asthma, chronic obstructive pulmonary diseases (COPD), respiratory infections, rhinitis, allergic rhinitis, nasal diseases and disorders; general and specific conditions, and systemic diseases with the lung or nasal cavity as the site of delivery Such medicaments include, but are not limited to, $\beta_2$-agonists, eg carmoterol, fenoterol, formoterol, levalbuterol, pirbuterol, reproterol, metaproterenol, rimiterol, salbutamol, salmeterol, indacaterol, terbutaline, orciprenaline, clenbuterol, bambuterol, procaterol, broxaterol, picumeterol, and bitolterol; non-selective β-stimulants such as ephedrine and isoprenaline; phosphodiesterase (PDE) inhibitors, eg methylxanthines, theophylline, aminophylline, choline theophyllinate, and selective PDE isoenzyme inhibitors, PDE 3 inhibitors, eg milrinone and motapizone; PDE 4 inhibitors, eg rolipram, cilomilast, roflumilast, oglemilast, and ONO 6126; PDE ¾ inhibitors, eg zardaverine and tolafentrine; inducers of HDAC2 eg theophylline; anticholinergics including muscarinic receptor (M1, M2, and M3) antagonists eg atropine, hyoscine, glycopyrrolate, ipratropium, tiotropium, oxitropium, NVA237, pirenzepine, and telenzepine; mast cell stabilisers, eg cromoglycate and ketotifen; bronchial antiinflammatory agents, eg nedocromil; steroids, eg beclometasone, dexamethasone, fluticasone, budesonide, flunisolide, rofleponide, triamcinolone, butixocort, mometasone, and ciclesonide; disease modifying agents such as methotrexate, leflunomide, teriflunomide, and hydroxychloroquine; histamine type 1 receptor antagonists, eg cetirizine, loratadine, desloratadine, fexofenadine, acrivastine, terfenadine, astemizole, azelastine, levocabastine, chlorpheniramine, promethazine, cyclizine, and mizolastine; antibacterial agents and agents for cystic fibrosis and/or tuberculosis treatment, eg Pseudomonas aeruginosa infection vaccines (eg Aerugen®), mannitol, denufosol, glutathione, N-acetylcysteine, amikacin duramycin, gentamycin, tobramycin, dornase alfa, alpha 1-antitrypsin, heparin, dextran, capreomycin, vancomycin, meropenem, ciprofloxacin, piperacillin, and rifampicin; mucolytic agents for the treatment of COPD and cystic fibrosis, eg N-acelylcysteine, and ambroxol; histamine type 2 receptor antagonists; tachykinin neurokinin antagonists; triptans, eg almotriptan, rizatriptan, naratriptan, zolmitriptan, sumatritpan, eletriptan, and frovatriptan; neurological agents eg apomorphine, dronabinol, dihydroergotamine, and loxapine; antiviral agents eg foscarnet, acyclovir, famciclovir, valacyclovir, ganciclovir, cidofovir; amantadine, rimantadine; ribavirin; zanamivir and oseltamavir and pleconaril, protease inhibitors (eg ruprintrivir, indinavir, nelfinavir, ritonavir, and saquinavir), nucleoside reverse transcriptase inhibitors (eg didanosine, lamivudine, stavudine, zalcitabine, and zidovudine), and non-nucleoside reverse transcriptase inhibitors (eg nevirapine and efavirenz); α-1/α-2 adrenoceptor agonists, eg propylhexedrine, phenylephrine, phenylpropanolamine, ephedrine, pseudophedrine, naphazoline oxymetazoline, tetrahydrozoline, xylometazoline, tramazoline, and ethylnorepinephrine; platelet aggregation inhibitors/anti-inflammatory agents, eg bemiparin, enoxaparin, heparin; anti-infectives, eg cephalosporins, penicillins, tetracyclines, macrolides, beta-lactams, flouroquinolones, streptomycin, sulphonamides, aminoglycosides (eg tobramycin), doripenem, pentamidine, colistimethate, and aztreonam; agents for sexual health, sexual dysfunction including premature ejaculation; eg. apomorphine, VR776, agents that acts via 5HT- and noradrenergic-mediated pathways in the brain, leuprolide, and PDE 5 inhibitors eg, sildenafil, tadalafil, and vardenafil; leukotriene modifiers, eg zileuton, fenleuton, tepoxalin, montelukast, zafirlukast, ontazolast, ablukast, pranlikast, verlukast, and iralukast; inducible nitric oxide synthase (iNOS) inhibitors; antifungals, eg amphotericin B, natamycin, and nystatin; analgesics, eg codeine, dihydromorphine, ergotamine, fentanyl, cannabinoids, and morphine; anxiolytic/antidepressive agents, eg benzodiazepines and benzodiazepine derivatives, diazepam, midazolam, chlordiazepoxide, lorazepam, oxazepam, clobazam, alprazolam, clonazepam, flurazepam, zolazepam; tryptase and elastase inhibitors; beta-2 integrin antagonists; adenosine receptor agonists or antagonists, eg adenosine 2α agonists; calcium channel blockers, eg gallopamil, and diltiazem; prostacyclin analogues, eg iloprost; endothelin-receptor antagonists, eg LU-135252; cytokine antagonists, eg chemokine antagonists and inhibitors and modifiers of cytokine synthesis including modifiers and inhibitors of the pro-inflammatory transcription factor, NFkB; interleukins and inhibitors of interleukins, eg aldesleukin; therapeutic proteins and peptides, eg insulin, insulin aspart, insulin glulisine; insulin lispro, neutral, regular and soluble insulins, isophane insulins, insulin zinc, protamine zinc insulin, insulin analogues, acylated insulin, insulin glargine, insulin detemir, glucagon, glucagon-like peptides, and exendins; enzymes, eg dornase alfa; systemically active macromolecules, eg human growth hormone, leuprolide, alpha-interferon, growth factors (eg insulin-like growth factor type 1), hormones, eg epinephrine, testosterone, and parathyroid hormone and analogues (eg Ostabolin-C); osteoporosis agents, eg bisphosphonates; anticancer agents, eg anthracyclines, doxorubicin, idarubicin, epirubicin, methotrexate, taxanes, paclitaxel, docetaxel, ciplatin, vinca alkaloids, vincristine, and 5-fluorouracil; anticoagulants, eg blood factors and blood factor constructs, eg FVIII-Fc and FIX-Fc; eg FV111-Fc; immunomodulators, eg cyclosporine, sirolimus, and tacrolimus; antiproliferative immunosuppressants, eg azathioprine, and mycophenolate mofetil; cytokines (eg interferons, interferon β, interleukins, and interleukin antagonists and inhibitors); nucleic acids; vaccines, eg flumist; anti-obesity agents; diagnostics and gene therapies. It will be clear to a person skilled in the art that, where appropriate, the medicaments may be linked to a carrier molecule or molecules and/or used in the form of prodrugs, salts, as esters, or as solvates to optimise the activity and/or stability of the medicament.

Inhalers having a blister piercing element according to the invention may also be used to deliver combinations of two or more different medicaments. Specific combinations of two medicaments which may be mentioned include combinations of steroids and β$_2$-agonists. Examples of such combinations are beclomethasone and formoterol; beclomethasone and salmeterol; fluticasone and formoterol; fluticasone and salmeterol; budesonide and formoterol; budesonide and salmeterol; flunisolide and formoterol; flunisolide and salmeterol; ciclesonide and salmeterol; ciclesonide and formoterol; mometasone and salmeterol; and mometasone and formoterol. Specifically inhalers according to the invention may also be used to deliver combinations of three different medicaments.

One aspect of the invention is directed to an inhalation device having a blister piercing element according to the invention and in which the plural of doses are contained in one reservoir. In another aspect of the invention, the inhalation device comprises the plural of doses in a multi-dose blister pack. In another aspect of the invention the inhalation device comprises the multi-dose blister pack in the form of a blister strip.

Accordingly, in a preferred embodiment the invention relates to an inhalation device having a blister piercing element according to the invention further comprising a housing and a blister strip, the strip being movable to sequentially align each blister with means for opening a blister to enable a user to inhale said dose, wherein each blister contains a pharmaceutical composition in powder form.

Many modifications and variations of the invention falling within the terms of the following claims will be apparent to those skilled in the art and the foregoing description should be regarded as a description of the preferred embodiments only.

The invention claimed is:

1. A blister piercing element for puncturing the lid of a blister containing a dose of medicament for inhalation by a user, comprising a body having a surface and an opening in the surface for the passage of air, or for the passage of medicament entrained in air, through the body, wherein the body includes a pair of spaced cutting teeth upstanding from the surface in spaced side-by-side relation, each cutting tooth projecting in cantilevered form over said opening, each tooth comprising an upright portion extending from the surface adjacent to, or from, a periphery of the opening and a cantilevered portion that extends from an upper end of the upright portion and projects out over said opening, each tooth having a distal cutting edge at a free end remote from said surface, each tooth further comprising an apex that lies on the distal cutting edge and which is configured for initially puncturing a blister lid, said distal cutting edge extending away from the apex of each tooth in two different directions and at an angle towards the surface, wherein a first part of the distal cutting edge of each tooth extends from the apex in a direction toward the apex of the other tooth and a second part of the distal cutting edge of each tooth extends from the apex in a direction away from the other tooth, a secondary cutting edge extending from the apex of each tooth along the cantilevered portion towards the upright portion, the distal cutting edge of each tooth being configured to initiate an initial slit in the blister lid initially punctured by the apex of each tooth and the secondary cutting edge configured to cut an initial slit in a direction extending away from the apex along the cantilevered portion towards the edge of the blister lid from which the tooth upstands when pressure is applied to the blister lid by the teeth, the teeth being spaced from each other so that the separate initial slits cut by the distal cutting edge of each tooth propagate in a direction toward each other between the teeth as the teeth continue to penetrate the blister lid, said pair of spaced cutting teeth thereby forming a single continuous slit when said initial slits are joined up as the teeth penetrate further through the blister lid, thereby defining a single flap which is folded into the blister by the teeth.

2. A blister piercing element according to claim 1, wherein the teeth are symmetrical about a plane extending between the teeth, which is perpendicular to the surface.

3. A blister piercing element according to claim 2, wherein the opening has first and second opposite edges and the teeth upstand from the surface adjacent to the first edge and project in cantilevered form in a direction towards the second edge to an extent that the distal cutting edge is closer to the second edge than to the first edge.

4. A blister piercing element according to claim 1, wherein it is the first distal cutting edge part of each tooth that is configured such that the initial slits cut by the distal cutting edge of each tooth propagate toward each other as the teeth penetrate a blister lid to form said single continuous slit extending between the apex of each tooth.

5. A blister piercing element according to claim 4, wherein said first distal cutting edge part of each tooth is configured so that the slit extending between the apex of each tooth is linear.

6. A blister piercing element according to claim 1, wherein the secondary cutting edge extends from the apex at an angle towards the surface.

7. A blister piercing element according to claim 1, wherein the secondary cutting edges of respective teeth extend at an angle away from each other.

8. A blister piercing element according to claim 1, wherein each tooth has a first angled facet bound by said first part of the distal cutting edge extending from the apex of a tooth towards the other tooth, and its secondary cutting edge.

9. A blister piercing element according to claim 8, wherein each tooth has a second angled facet bound by said second part of the distal cutting edge extending from the apex of a tooth in a direction away from the other tooth, and its secondary cutting edge.

10. A blister piercing element according to claim 1, wherein the first part of the distal cutting edge of each tooth extends from the apex towards said surface at an angle which is smaller than the angle at which the second part of the distal cutting edge of each tooth extends from the apex towards said surface, said angle being defined with respect to a direction defined by the intersection of a plane parallel to the surface with a plane perpendicular to the surface and comprising said first/second part of the distal cutting edge.

11. A blister piercing element according to claim 1, wherein the opening in the surface comprises a first opening and the pair of spaced cutting teeth comprise a first pair of spaced cutting teeth, the body comprising a second opening in the surface, a second pair of spaced cutting teeth upstanding from the surface in spaced side-by-side relation, each cutting tooth projecting in cantilevered form over said second opening, each tooth comprising an upright portion extending from the surface adjacent to, or from, a periphery of the second opening and a cantilevered portion that extends from an upper end of the upright portion and projects out over said second opening, each tooth having a distal cutting edge at a free end remote from said surface, each tooth further comprising an apex that lies on the distal cutting edge and which is configured for initially puncturing a blister lid, said distal cutting edge extending away from the apex of each tooth in two different directions and at an angle towards the surface, wherein a first part of the distal cutting edge of each tooth extends from the apex in a direction toward the apex of the other tooth and a second part of the distal cutting edge of each tooth extends from the apex in a direction away from the other tooth, a secondary cutting edge extending from the apex of each tooth along the cantilevered portion towards the upright portion, the distal cutting edge of each second tooth being configured to initiate an initial slit in the blister lid initially punctured by the apex of each tooth and the secondary cutting edge configured to cut an initial slit in a direction extending away from the apex along the cantilevered portion towards the edge of the blister lid from which the tooth up stands when pressure is applied to the blister lid by the second teeth at the same time pressure is applied to the blister lid by the first teeth, the second teeth being spaced from each other so that an initial slit cut by the distal cutting edge of each second tooth propagates in a direction toward each other between the second teeth as the second teeth continue to enter the blister so that a single continuous slit is formed when said initial slits are joined up in the blister lid by said second pair of spaced cutting teeth to define a single flap that is folded into the blister by the second teeth.

12. A blister piercing element according to claim 11, wherein the first and second pairs of spaced cutting teeth are positioned in back-to-back relation so that the first pair of spaced cutting teeth project in cantilevered form over the first opening in an opposite direction to the direction in which the second pair of spaced cutting teeth project in cantilevered form over the second opening.

13. A blister piercing element according to claim 12, wherein the body has a flow channel extending from the second opening to direct drug laden air that has passed through the second opening into a mouthpiece of a dry powder inhalation device.

14. An inhalation device having a blister piercing element according to claim 1.

* * * * *